┌────────────────────────────────────────────────┐
│ 
│ US006159720A

United States Patent [19]
Murashima et al.

[11] Patent Number: 6,159,720
[45] Date of Patent: Dec. 12, 2000

[54] ENZYME ENDOGLUCANASE AND CELLULASE PREPARATIONS CONTAINING THE SAME

[75] Inventors: Kouichirou Murashima, Sakado; Tatsuki Moriya, Odawara; Toru Hamaya; Jinichiro Koga, both of Sakado; Naomi Sumida, Odawara; Kaoru Aoyagi, Odawara; Takeshi Murakami, Odawara; Toshiaki Kono, Sakado, all of Japan

[73] Assignee: Meiji Seika Kaisha, Ltd., Tokyo, Japan

[21] Appl. No.: 09/230,222

[22] PCT Filed: Jul. 24, 1997

[86] PCT No.: PCT/JP97/02561

§ 371 Date: Mar. 3, 1999

§ 102(e) Date: Mar. 3, 1999

[87] PCT Pub. No.: WO98/03640

PCT Pub. Date: Jan. 29, 1998

[30] Foreign Application Priority Data

Jul. 24, 1996 [JP] Japan ................... 8-194974

[51] Int. Cl.⁷ .............. C12N 9/42; C12N 15/56; C12S 11/00
[52] U.S. Cl. ............ 435/209; 435/200; 435/263; 435/264; 435/277; 435/278; 435/320.1; 435/252.3; 435/89.1; 536/23.1; 536/23.2

[58] Field of Search ................... 435/264, 200, 435/263, 277, 278, 209, 320.1, 69.1, 252.3; 536/23.1, 23.2

[56] References Cited

U.S. PATENT DOCUMENTS 5,435,809  7/1995  Holst et al. .................. 8/401

FOREIGN PATENT DOCUMENTS

WO 91/17243  11/1991  Denmark ............... 9/42
9600787  1/1996  European Pat. Off. .
9617994  6/1996  European Pat. Off. .
8501692  2/1996  Japan .

OTHER PUBLICATIONS

Charlotte Schou, et al., "Stereochemistry, specificity and kinetics of the hydrolysis of reduced cellodextrins by nine cellulases" Eur. J. Biochem., 1993, vol. 217, p. 947–953.

*Primary Examiner*—Rebecca E. Prouty
*Assistant Examiner*—Richard Hutson
*Attorney, Agent, or Firm*—Varndell & Varndell, PLLC

[57] ABSTRACT

A highly active cellulase suitable for use in a removal of nap of cellulose-containing fibers, a process for reducing cellulose-containing fibers and a process for decoloring denim-dyed cellulose-containing fibers, and its gene are provided. A novel cellulase NCE4 isolated from Humicola insolens is a highly active cellulase, and can be used for various treatments of cellulose-containing fibers.

19 Claims, No Drawings

SEQUENCE LISTING

```
<160> NUMBER OF SEQ ID NOS: 31

<210> SEQ ID NO 1
<211> LENGTH: 305
<212> TYPE: PRT
<213> ORGANISM: Humicola insolens

<400> SEQUENCE: 1

Met Arg Ser Ser Pro Leu Leu Arg Ser Ala Val Val Ala Ala Leu Pro
    -20                 -15                 -10

Val Leu Ala Leu Ala Ala Asp Gly Lys Ser Thr Arg Tyr Trp Asp Cys
 -5              -1   1                   5                  10

Cys Lys Pro Ser Cys Gly Trp Ala Lys Lys Ala Pro Val Asn Gln Pro
             15                  20                  25

Val Phe Ser Cys Asn Ala Asn Phe Gln Arg Leu Thr Asp Phe Asp Ala
         30                  35                  40

Lys Ser Gly Cys Glu Pro Gly Gly Val Ala Tyr Ser Cys Ala Asp Gln
     45                  50                  55

Thr Pro Trp Ala Val Asn Asp Asp Phe Ala Phe Gly Phe Ala Ala Thr
 60                  65                  70                  75

Ser Ile Ala Gly Ser Asn Glu Ala Gly Trp Cys Cys Ala Cys Tyr Glu
                 80                  85                  90
```

-continued

```
Leu Thr Phe Thr Ser Gly Pro Val Ala Gly Lys Lys Met Val Val Gln
             95                 100                 105

Ser Thr Ser Thr Gly Gly Asp Leu Gly Ser Asn His Phe Asp Leu Asn
         110                 115                 120

Ile Pro Gly Gly Val Gly Ile Phe Asp Gly Cys Thr Pro Gln Phe
     125                 130                 135

Gly Gly Leu Pro Gly Gln Arg Tyr Gly Gly Ile Ser Ser Arg Asn Glu
140                 145                 150                 155

Cys Asp Arg Phe Pro Asp Ala Leu Lys Pro Gly Cys Tyr Trp Arg Phe
                 160                 165                 170

Asp Trp Phe Lys Asn Ala Asp Asn Pro Ser Phe Ser Phe Arg Gln Val
             175                 180                 185

Gln Cys Pro Ala Glu Leu Val Ala Arg Thr Gly Cys Arg Arg Asn Asp
         190                 195                 200

Asp Gly Asn Phe Pro Ala Val Gln Ile Pro Ser Ser Ser Thr Ser Ser
     205                 210                 215

Pro Val Gly Gln Pro Thr Ser Thr Ser Thr Thr Ser Thr Ser Thr Thr
220                 225                 230                 235

Ser Ser Pro Pro Val Gln Pro Thr Thr Pro Ser Gly Cys Thr Ala Glu
                 240                 245                 250

Arg Trp Ala Gln Cys Gly Gly Asn Gly Trp Ser Gly Cys Thr Thr Cys
             255                 260                 265

Val Ala Gly Ser Thr Cys Thr Lys Ile Asn Asp Trp Tyr His Gln Cys
         270                 275                 280

Leu
```

```
<210> SEQ ID NO 2
<211> LENGTH: 1257
<212> TYPE: DNA
<213> ORGANISM: Humicola insolens
<220> FEATURE:
<221> NAME/KEY: sig_peptide
<222> LOCATION: (118)..(180)
<220> FEATURE:
<221> NAME/KEY: CDS
<222> LOCATION: (118)..(180)
<220> FEATURE:
<221> NAME/KEY: mat_peptide
<222> LOCATION: (181)..(1088)
<220> FEATURE:
<221> NAME/KEY: CDS
<222> LOCATION: (181)..(452)
<220> FEATURE:
<221> NAME/KEY: intron
<222> LOCATION: (453)..(508)
<220> FEATURE:
<221> NAME/KEY: CDS
<222> LOCATION: (509)..(1088)

<400> SEQUENCE: 2
aatgacgggg caacctcccg cccgggccca actcttgggt ttggtttgac aggccgtctg      60
tctcttgcgt cctcttacta cgcctgcctg gaccctacgt ctcaactccg attcaag       117 atg cgt tcc tcc cct ctc ctc cgc tcc gcc gtt gtg gcc gcc ctg ccg     165
Met Arg Ser Ser Pro Leu Leu Arg Ser Ala Val Val Ala Ala Leu Pro
    -20                 -15                 -10 gtg ttg gcc ctt gcc gct gat ggc aag tcc acc cgc tac tgg gac tgc     213
Val Leu Ala Leu Ala Ala Asp Gly Lys Ser Thr Arg Tyr Trp Asp Cys
 -5          -1   1               5                  10 tgc aag cct tcg tgc ggc tgg gcc aag aag gct ccc gtg aac cag cct     261
```

```
                Cys Lys Pro Ser Cys Gly Trp Ala Lys Lys Ala Pro Val Asn Gln Pro
                            15                  20                  25 gtc ttc tcc tgc aac gcc aac ttc cag cgt ctc act gac ttc gac gcc         309
Val Phe Ser Cys Asn Ala Asn Phe Gln Arg Leu Thr Asp Phe Asp Ala
                30                  35                  40 aag tcc ggc tgc gag ccg ggc ggt gtc gcc tac tcg tgc gcc gac cag         357
Lys Ser Gly Cys Glu Pro Gly Gly Val Ala Tyr Ser Cys Ala Asp Gln
            45                  50                  55 acc cca tgg gct gtg aac gac gac ttc gcg ttc ggt ttt gct gcc acc         405
Thr Pro Trp Ala Val Asn Asp Asp Phe Ala Phe Gly Phe Ala Ala Thr
60                  65                  70                  75 tct att gcc ggc agc aat gag gcg ggc tgg tgc tgc gcc tgc tac ga          452
Ser Ile Ala Gly Ser Asn Glu Ala Gly Trp Cys Cys Ala Cys Tyr Glu
                80                  85                  90 gtaagctttg gtcgcgtgtg taacactgtg caggcatagc actaaccacc tcccag g         509 ctc acc ttc aca tcc ggt cct gtt gct ggc aag aag atg gtc gtc cag         557
Leu Thr Phe Thr Ser Gly Pro Val Ala Gly Lys Lys Met Val Val Gln
                95                  100                 105 tcc acc agc act ggc ggt gat ctt ggc agc aac cac ttc gat ctc aac         605
Ser Thr Ser Thr Gly Gly Asp Leu Gly Ser Asn His Phe Asp Leu Asn
            110                 115                 120 atc ccc ggc ggc ggc gtc ggc atc ttc gac gga tgc act ccc cag ttc         653
Ile Pro Gly Gly Gly Val Gly Ile Phe Asp Gly Cys Thr Pro Gln Phe
        125                 130                 135 ggc ggt ctg ccc ggc cag cgc tac ggc ggc atc tcg tcc cgc aac gag         701
Gly Gly Leu Pro Gly Gln Arg Tyr Gly Gly Ile Ser Ser Arg Asn Glu
140                 145                 150                 155 tgc gat cgg ttc ccc gac gcc ctc aag ccc ggc tgc tac tgg cgc ttc         749
Cys Asp Arg Phe Pro Asp Ala Leu Lys Pro Gly Cys Tyr Trp Arg Phe
                160                 165                 170 gac tgg ttc aag aac gcc gac aac ccg agc ttc agc ttc cgt cag gtc         797
Asp Trp Phe Lys Asn Ala Asp Asn Pro Ser Phe Ser Phe Arg Gln Val
            175                 180                 185 caa tgc cca gcc gag ctc gtc gct cgc acc gga tgc cgc cgc aac gac         845
Gln Cys Pro Ala Glu Leu Val Ala Arg Thr Gly Cys Arg Arg Asn Asp
        190                 195                 200 gac ggc aac ttc cct gcc gtc cag atc ccc tcc agc agc acc agc tct         893
Asp Gly Asn Phe Pro Ala Val Gln Ile Pro Ser Ser Ser Thr Ser Ser
205                 210                 215 ccg gtc ggc cag cct acc agt acc agc acc acc tcc acc tcc acc acc         941
Pro Val Gly Gln Pro Thr Ser Thr Ser Thr Thr Ser Thr Ser Thr Thr
220                 225                 230                 235 tcg agc ccg ccc gtc cag cct acg act ccc agc ggc tgc act gct gag         989
Ser Ser Pro Pro Val Gln Pro Thr Thr Pro Ser Gly Cys Thr Ala Glu
                240                 245                 250 agg tgg gct cag tgc ggc ggc aat ggc tgg agc ggc tgc acc acc tgc         1037
Arg Trp Ala Gln Cys Gly Gly Asn Gly Trp Ser Gly Cys Thr Thr Cys
```

```
                    255                 260                 265
gtc gct ggc agc acc tgc acg aag att aat gac tgg tac cat cag tgc      1085
Val Ala Gly Ser Thr Cys Thr Lys Ile Asn Asp Trp Tyr His Gln Cys
                    270                 275                 280 ctg taa acgcaggca gcctgagaac cttactggtt gcgcaacgaa atgcactcc         1141
Leu caatcactgt attagttctt gtacataatt tcgtcatccc tccagggatt gtcacatata    1201
tgcaatgatg aatactgaac acaaacctgg ccgcttgaac tggccgaagg aatgcc        1257

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: N-TERMINAL
      AMINO ACID SEQUENCE

<400> SEQUENCE: 3

Ala Asp Gly Lys Ser Thr Arg Tyr Trp Asp Cys Cys Lys Pro Ser
 1               5                  10                  15

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: PEPTIDE
      FRAGMENTS

<400> SEQUENCE: 4

Tyr Gly Gly Ile Ser Ser
 1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: PEPTIDE
      FRAGMENTS

<400> SEQUENCE: 5

Phe Pro Asp Ala Leu Lys
 1               5

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: PEPTIDE
      FRAGMENTS

<400> SEQUENCE: 6

Phe Asp Trp Phe Lys Asn Ala Asp Asn Pro Ser Phe Ser Phe Arg
 1               5                  10                  15

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: PRIMER
<220> FEATURE:
```

```
<221> NAME/KEY: modified_base
<222> LOCATION: (3)
<223> OTHER INFORMATION: i
<220> FEATURE:
<221> NAME/KEY: modified_base
<222> LOCATION: (9)
<223> OTHER INFORMATION: i
<220> FEATURE:
<221> NAME/KEY: base
<222> LOCATION: (15)
<223> OTHER INFORMATION: a, g, c or t

<400> SEQUENCE: 7
gcngayggna artcnac                                                    17

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: PRIMER
<220> FEATURE:
<221> NAME/KEY: modified_base
<222> LOCATION: (3)
<223> OTHER INFORMATION: i
<220> FEATURE:
<221> NAME/KEY: modified_base
<222> LOCATION: (9)
<223> OTHER INFORMATION: i

<400> SEQUENCE: 8
gcngayggna aragyac                                                    17

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: PRIMER
<220> FEATURE:
<221> NAME/KEY: modified_base
<222> LOCATION: (2)
<223> OTHER INFORMATION: i

<400> SEQUENCE: 9
cngcrttytt raaccartc                                                  19

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: PRIMER

<400> SEQUENCE: 10
gtgatgaggg ctggcgacag gcc                                             23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: PRIMER

<400> SEQUENCE: 11
ctgccacctc tattgccggc agc                                             23

<210> SEQ ID NO 12
<211> LENGTH: 23
```

```
<212> TYPE: DNA
<213> ORGANISM: Artificial Sequence
<220> FEATURE:
<223> OTHER INFORMATION: Description of Artificial Sequence: PRIMER

<400> SEQUENCE: 12
cccgacgccc tcaagcccgg ctg                                              23

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: PRIMER

<400> SEQUENCE: 13
ggctggagcg gctgcaccac ctg                                              23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: PRIMER

<400> SEQUENCE: 14
gacctgacgg aagctgaagc tcg                                              23

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: PRIMER

<400> SEQUENCE: 15
agcagtgcag ccgctgggag tcg                                              23

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: PRIMER

<400> SEQUENCE: 16
tggcagatga ggacgtggtg ttg                                              23

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: PRIMER

<400> SEQUENCE: 17
cgcagccgga cttggcgtcg aag                                              23

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: PRIMER

<400> SEQUENCE: 18
```

```
atgcgttcct cccctctcct ccgctccgcc                                30
```

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: PRIMER

<400> SEQUENCE: 19

```
tacaggcact gatggtacca gtcattaatc                                30
```

<210> SEQ ID NO 20
<211> LENGTH: 36
<212> TYPE: DNA
<213> ORGANISM: Artificial Sequence
<220> FEATURE:
<223> OTHER INFORMATION: Description of Artificial Sequence: PRIMER

<400> SEQUENCE: 20

```
gagcgccaga actgtggatc cacttggtga gcaatg                         36
```

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence: PRIMER

<400> SEQUENCE: 21

```
tccgccgttc tgagcggatc caggcgtttg gcgcg                          35
```

<210> SEQ ID NO 22
<211> LENGTH: 36
<212> TYPE: DNA
<213> ORGANISM: Artificial Sequence
<220> FEATURE:
<223> OTHER INFORMATION: Description of Artificial Sequence: PRIMER

<400> SEQUENCE: 22

```
gccgcccagc aggcgggatc cctcaccacc gagagg                         36
```

<210> SEQ ID NO 23
<211> LENGTH: 36
<212> TYPE: DNA
<213> ORGANISM: Artificial Sequence
<220> FEATURE:
<223> OTHER INFORMATION: Description of Artificial Sequence: PRIMER

<400> SEQUENCE: 23

```
tgatcgtcga gtcagggatc cagaatttac aggcac                         36
```

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: N-TERMINAL
      AMINO ACID SEQUENCE

<400> SEQUENCE: 24

```
Asn Cys Gly Ser Leu Thr Thr Glu Arg His Pro Ser Leu Ser Trp
 1               5                  10                  15
```

<210> SEQ ID NO 25
<211> LENGTH: 30

```
<212> TYPE: DNA
<213> ORGANISM: Artificial Sequence
<220> FEATURE:
<223> OTHER INFORMATION: Description of Artificial Sequence: PRIMER

<400> SEQUENCE: 25
ccggtgttgg ccggatccgc tgatggcaag                              30

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: PRIMER

<400> SEQUENCE: 26
taaggccctc aaggatccct gcgtctacag                              30

<210> SEQ ID NO 27
<211> LENGTH: 20
<212> TYPE: PRT
<213> ORGANISM: Artificial Sequence
<220> FEATURE:
<223> OTHER INFORMATION: Description of Artificial Sequence: N-TERMINAL
      AMINO ACID SEQUENCE

<400> SEQUENCE: 27

Val Val Glu Glu Arg Gln Asn Cys Gly Ser Ala Asp Gly Lys Ser Thr
 1               5                  10                  15
Arg Tyr Trp Asp
            20

<210> SEQ ID NO 28
<211> LENGTH: 20
<212> TYPE: PRT
<213> ORGANISM: Artificial Sequence
<220> FEATURE:
<223> OTHER INFORMATION: Description of Artificial Sequence: N-TERMINAL
      AMINO ACID SEQUENCE

<400> SEQUENCE: 28

Asn Cys Gly Ser Ala Asp Gly Lys Ser Thr Arg Tyr Trp Asp Cys Cys
 1               5                  10                  15
Lys Pro Ser Cys
            20

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: PRIMER

<400> SEQUENCE: 29
gtcatgaagc ttcattaagg tacgtatgca ac                           32

<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: PRIMER

<400> SEQUENCE: 30
ggtgatggat ccggcctgct gggcagcgac gc                           32
```

```
<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: N-TERMINAL
      AMINO ACID SEQUENCE

<400> SEQUENCE: 31

Gln Ala Gly Ser Ala Asp Gly Lys Ser Thr Arg Tyr Trp Asp Cys
1               5                  10                  15
```

ENZYME ENDOGLUCANASE AND CELLULASE PREPARATIONS CONTAINING THE SAME

BACKGROUND OF THE INVENTION

1. Field of the Invention

The present invention relates to cellulase and a cellulase preparation containing the same, as well as a removal of nap of cellulose-containing fibers, a process for reducing cellulose-containing fibers and a process for decoloring denim-dyed cellulose-containing fibers by using the cellulase or cellulase preparation.

2. Background Art

Cellulose-containing fibers are treated with cellulase to give desired properties to those fibers. For example, in the fiber industry, treatment is performed using cellulase in order to improve the texture and appearance of cellulose-containing fibers, and to give the appearance of being stonewashed to denim-dyed cellulose-containing fibers.

In addition, Tencel, a reproduced cellulose fiber that is spun wood pulp-based cellulose dissolved in an organic solvent, has attracted attention in recent years due to properties such as high strength, water absorbing capacity and the like, and its manufacturing method which causes very little environmental contamination. However, since nap is produced during the manufacturing process of Tencel, Tencel has low product value as a fiber if left as is. Therefore, methods for removing nap formed during the manufacturing process by using cellulase have been proposed.

At present, cellulases primarily originating in Trichoderma species and Humicola species of wood-rotting fungi are used for treatment of cellulose-containing fibers. However, a large amount of cellulase is required under the present conditions to demonstrate the desired effect on the fibers.

It is likely that the cost of this processing would be able to be reduced, if it were possible to be able to improve the texture and appearance of cellulose-containing fibers, give the appearance of being stone-washed to denim-dyed cellulose-containing fibers, and remove nap from Tencel by using highly active cellulase in smaller amount than the conventional amount.

Furthermore, an example of a cellulase originating in Humicola, it is shown in WO 91/17243 (Japanese Patent Laid-Open Publication No. 5-509223) that the endoglucanase gene of 43 kD was isolated from Humicola insolens DSM1800 strain, and that its base sequence was determined.

SUMMARY OF THE INVENTION

The inventors of the present invention have now isolated from Humicola insolens a novel highly active cellulase and its gene, which can be used extremely advantageously in the treatment of various cellulose-containing fibers. The present invention is based on those findings.

Thus, an object of the present invention is to provide a novel cellulase and its gene.

Moreover, another object of the present invention is to provide a process for removing nap of cellulose-containing fibers using a novel cellulase, a process for reducing cellulose-containing fibers and a process for decoloring denim-dyed, cellulose-containing fibers.

The novel cellulase according to the present invention is a protein or a modified protein having a portion of an amino acid sequence shown in SEQ ID No. 1 or a sequence from position 1 to position 284 of the amino acid sequence shown in SEQ ID No. 1.

In addition, according to the present invention, there is provided a process for removing nap of cellulose-containing fibers, a process for reducing cellulose-containing fibers, and a process for decoloring denim-dyed, cellulose-containing fibers comprising the step of contacting the protein or modified protein of the present invention with the denim-dyed, cellulose-containing fibers.

DETAILED DESCRIPTION OF THE INVENTION

Microorganism Deposition

E. coli JM109 strain transformed by plasmid pNCE4Sal (see Example A5) containing the cellulase gene according to the present invention has been deposited in the National Institute of Bioscience and Human-Technology, Ministry of International Trade and Industry (1-1-3 Higashi, Tsukuba-shi, Ibaraki-ken, Japan) under accession No. FERM BP-5976 (original deposit: FERM P-15732, date of original deposit: Jul. 12, 1996).

Cellulase and its Gene

The cellulase enzyme according to the present invention is a protein having a portion or a sequence from position 1 to position 284 of the sequence shown in SEQ ID No. 1. In the present invention, a portion of the sequence shown in SEQ ID No. 1 refers to a partial sequence, for example, that has a length available for a probe, or that still maintains cellulase activity, particularly endoglucanase activity.

In addition, the present invention also includes a protein having a portion or all of the amino acid sequence from position −21 to position −1 of SEQ ID No. 1 on the N-terminal of the above protein. The amino acid sequence from position −21 to position −1 of SEQ ID No.1 is considered to be a signal peptide. Therefore, in addition to the partial sequence that retains signal peptide activity, a portion of the sequence includes the sequence that remains on the N-terminal as a result of the processing in which the processing position may vary depending on the type of a host.

Moreover, modified proteins of the above protein are also encompassed by the scope of the present invention. In the present invention, a modified protein refers to a protein in which a modification, such as the addition, insertion, deletion or substitution of one or a plurality of amino acids, has occurred in the amino acid sequence of the protein, while still retaining cellulase activity, particularly endoglucanase activity.

The sequence from position 1 to position 284 of the amino acid sequence shown in SEQ ID No. 1 is hereinafter referred to as cellulase NCE4, and its gene is referred to as the cellulase NCE4 gene.

The cellulase according to the present invention has high activity, and thus allows for the desired effects in various uses even in small amounts. For example, according to a preferred embodiment of the present invention, in comparison with crude cellulase prepared from a culture liquid of Humicola insolens, NCE4 shows equivalent nap removal effects on cellulose fibers at a protein mass of about 1/100 that of the crude cellulase, equivalent denim-dyed cellulose-containing fiber decoloring effects at a protein mass about 1/25, and equivalent cellulose fiber reduction effects at a protein mass of about 1/5. Accordingly, it can be used for more efficient and economical treatment of cellulose fibers.

According to another embodiment of the present invention, there is provided a DNA sequence that codes for the amino acid sequence of the above protein. A typical sequence of the DNA sequence has a portion or all of the base sequence shown in SEQ ID No. 2.

The base sequence shown in SEQ ID No. 2 has an open reading frame starting at ATG at positions 118 to 120 and terminating at TAA at positions 1089 to 1091. In addition, the base sequence from position 181 to position 1088 corresponds to the mature protein composed of 284 residues. Moreover, the presence of an intron has been confirmed in the base sequence of SEQ ID No. 2 (see Example A7).

When the amino acid sequence of a protein is given, the DNA sequence coding for that sequence is easily defined, and various base sequences that code for a portion or all of the amino acid sequence shown in SEQ ID No. 1 can be selected. Thus, a DNA sequence coding for a portion or all of the amino acid sequence shown in SEQ ID No. 1 according to the present invention refers to a sequence having any degenerate codons coding for the same amino acids in a base sequence, in addition to a portion or all of the base sequence shown in SEQ ID No. 2.

The DNA according to the present invention may be of natural origin or be completely synthesized. In addition, it may also be synthesized using a portion of DNA of natural origin. Typical methods for obtaining DNA include a method of obtaining the DNA from a Humicola insolens chromosome library or cDNA library routinely employed in the field of genetic engineering, an example of which includes screening using a suitable DNA probe prepared based on information about a partial amino acid sequence. In addition, the DNA can also be obtained from the deposited microorganism described above.

Expression Vector and Transformed Microorganism

According to the present invention, there is provided an expression vector that contains the DNA sequence according to the present invention in a state that allows the DNA sequence to replicate within a host microorganism and to express a protein encoded by the DNA sequence. Moreover, according to the present invention, there is provided a microorganism that is transformed by the expression vector. There are no particular limitations on this host-vector system, and for example, systems using E. coli, Actinomycetes, yeast or molds, as well as fused protein expression systems with other proteins using these microorganisms, can be used. Methods routinely employed in the field of genetic engineering can be used for the procedure and method for constructing the vector according to the present invention.

The expression vector of the present invention may contain, in addition to the DNA sequence of the present invention, a DNA sequence that controls the expression of a desired protein or a selectable marker to ensure the introduction of the vector into a host and the expression of the desired protein. Since the base sequence of SEQ ID No.2 is considered to contain the regulatory sequence, the use of this base sequence may be advantageous. In addition, the expression vector of the present invention may contain DNA sequences that code for cellulase in a repetitive form (tandem). The expression vector of the present invention that contains the DNA sequence of the present invention may be constructed in accordance with routine methods. In addition, transformation of a microorganism by the expression vector of the present invention may also be carried out in accordance with methods routinely employed in the art.

The transformant of the present invention can be cultured in a suitable medium. The protein according to the present invention can be isolated from this culture. Thus, according to another embodiment of the present invention, there is provided a method for preparing the novel protein of the present invention. The culturing of the transformants and its conditions may be basically similar to those of the microorganism used. In addition, recovery and purification of the novel protein according to the present invention from the culture can be performed in accordance with routine methods.

Cellulase Applications/Cellulase Preparation

The cellulase according to the present invention is used in various applications in its original form or as a cellulase preparation. In particular, it is used to give desired properties to cellulose fibers. More specifically, it is used for removing nap of cellulose-containing fibers, performing weight reduction processing, and performing decoloring processing of denim-dyed, cellulose-containing fibers.

A cellulase preparation may be prepared by mixing the cellulase according to the present invention with ingredients generally contained in cellulase preparations, examples of which include excipients (e.g., lactose, sodium chloride, sorbitol), surfactants and antiseptics.

A process for removing nap of cellulose-containing fibers, a process for reducing cellulose-containing fibers, and a process for decoloring denim-dyed, cellulose-containing fibers using the cellulase or cellulase preparation according to the present invention can be carried out by contacting the cellulase of the present invention with cellulose-containing fibers.

Although contact temperature, the amount of cellulase and other conditions may be decided depending on various conditions in a system, for example, in nap removal of cellulose-containing fibers, treatment can be performed at about 50–60° C. using cellulase at a protein concentration of 5–50 mg/liter. In the process for reducing cellulose-containing fibers, treatment can be performed at about 50–60° C. using cellulase at a protein concentration of 100–300 mg/liter. Moreover, in the process for decoloring denim-dyed, cellulose-containing fibers, treatment can be performed at about 50–60° C. using cellulase at a protein concentration of 2–10 mg/liter.

EXAMPLES

The present invention will be further explained in view of the following examples that are not meant to limit the invention.

Example A1: Isolation and Purification of an Ingredient Having the Tencel Nap Removing Activity from Humicola Insolens Humicola insolens MN200-1 was cultured at 37° C. in (N) medium (5.0% Avicel, 2.0% yeast extract, 0.1% polypeptone, 0.03% calcium chloride, 0.03% magnesium sulfate, pH 6.8). After culturing for 7 days, by centrifuging the resulting culture liquid at 7000 rpm for 20 minutes, the microorganisms were removed and the culture supernatant was used as the crude cellulase preparation.

This crude cellulase preparation was applied to hydrophobic chromatography (Phenyl-Sepharose High-Performance 16/100, Pharmacia-Biotech), and fractionated by eluting with aqueous ammonium sulfate over a concentration gradient of 1 to 0 M in 50 mM phosphate buffer (pH 7.0). Since potent Tencel nap removing activity was observed in the fraction obtained during a concentration gradient of 0.1 to 0 M, that fraction was again applied to hydrophobic chromatography (Phenyl-Sepharose High-Performance 16/100) and eluted with aqueous ammonium sulfate over a concentration gradient of 0.4 to 0 M in 50 mM phosphate buffer (pH 7.0) followed by removal of the active fraction.

Then, this fraction was applied to reversed-phase chromatography (Source 15 ISO, Pharmacia-Biotech) and fractionated by eluting with aqueous ammonium sulfate over a concentration gradient of 1 to 0 M in 50 mM phosphate buffer (pH 7.0). Since the fraction obtained during a concentration of 0 M was observed to exhibit potent Tencel nap removing activity, that fraction was further applied to reversed-phase chromatography (Source 15 PHE, Pharmacia-Biotech), eluted with aqueous ammonium sulfate over a concentration gradient of 1 to 0 M in 50 mM phosphate buffer (pH 7.0), and the fraction exhibiting potent Tencel nap removing activity was isolated as purified enzyme NCE4. This NCE4 exhibited a single band at a molecular weight of 43 kDa in SDS-PAGE.

Example A2: Partial Amino Acid Sequence of Cellulase NCE4

(1) Identification of N-terminal amino acid residues

Column chromatography (column: RESOURCE (Trade name) RPC 3 ml, 5–60% acetonitrile gradient containing 0.1% TFA) was performed with an FPLC system (Pharmacia-Biotech) followed by removal of the main peak to determine the N-terminal amino acid sequence of the protein purified in Example 1.

After lyophilizing the above fraction, it was dissolved in a small amount of water followed by electrophoresis using 8% Gel SDS-PAGE Mini (TEFCO). After electrically transferring the protein to PVDF membrane (Millipore) using a Multiphore II electrophoresis system (Pharmacia-Biotech), and staining with Coomassie brilliant blue R-250 (Nakalaitesque), the membrane was decolored, washed with water and air dried. The portion at which the protein having a molecular weight of 43 kDa was blotted was cut out and applied to the Model 492 Protein Sequencer (Perkin-Elmer) to determine 15 residues of the N-terminal amino acid sequence. The resulting sequence was as shown below.

N-terminal amino acid sequence: Ala-Asp-Gly-Lys-Ser-Thr-Arg-Tyr-Trp-Asp-(Cys)-Lys-Pro-Ser (15 residues) (SEQ ID NO:3)

(2) Peptide Mapping

After lyophilizing the protein purified by FPLC in (1) above, it was dissolved in 100 mM ammonium bicarbonate buffer (pH 8.0). Approximately 1/20 mole volume of trypsin (Promega) relative to the amount of protein was added and allowed to react for 48 hours at 37° C. Column chromatography (column: C8 220×2.1 mm, 0.1% TFA, 0% acetonitrile to 0.085% TFA, 35% acetonitrile gradient) was performed on this dissolution product with the Model 172μ Preparative HPLC System (Perkin-Elmer) to obtain three types of peptides. The amino acid sequences of the resulting peptide fragments were determined using the above protein sequencer. Those results were as shown below.

TP-1: Tyr-Gly-Gly-Ile-Ser-Ser (6 residues) (SEQ ID NO:4)

TP-2: Phe-Pro-Asp-Ala-Leu-Lys (6 residues) (SEQ ID NO:5)

TP-3: Phe-Asp-Trp-Phe-Lys-Asn-Ala-Asp-Asn-Pro-Ser-Phe-Ser-Phe-Arg (15 residues) (SEQ ID NO:6)

Since the N-terminal amino acid sequence and amino acid sequences obtained by peptide mapping exhibit homology with the amino acid sequence of 43 kDa endoglucanase obtained from Humicola insolens DSM1800 shown in WO 91/17243 (Japanese Patent Laid-Open Publication No. 5-509223), this protein was strongly suggested to be a type of cellulase.

In addition, when the above sequences were compared with the sequences registered in Protein Identification Resource (PIR), R44.0, March 1995 or those registered in SWISS-PROT R31.0, March 1995, although the above sequences exhibited homology with some registered sequences, they were not identical, thus clearly indicating the protein obtained herein to be a novel protein.

Example A3: Construction of Genome DNA Library

Isolation of genome DNA was performed in accordance with the method of Horiuchi, et al. (Hiroyuki Horiuchi et al., J. Bacteriol., 170:272–278, 1988).

To begin with, Humicola insolens MN200-1 was cultured in the above (N) medium at 37° C. After culturing for 2 days, the microorganisms were collected by centrifugation (3500 rpm, 10 minutes). The resulting microorganisms were treated with phenol, proteinase K and ribonuclease A followed by polyethylene glycol (PEG) precipitation to obtain genome DNA.

Then, Humicola insolens genome DNA was digested by Sau3A I, and after confirming partial digestion within a range of 9–23 kbp by agarose gel electrophoresis, the DNA fragments were collected by ethanol precipitation. The DNA fragments were then ligated to a phage vector and the BamH I arm of an EMBL3 cloning kit (Stratagene) using T4 ligase (Toyobo Co., Ltd.). After subjecting this to ethanol precipitation, the precipitate was dissolved in TE (10 mM Tris-HCl (pH 8.0), 1 mM EDTA) buffer.

The entire amount of ligated mixture was packaged in a lambda head using package components frozen as described in the method of Hohn, B. (Hohn, B., Methods Enzymol., 68:299–309, 1979) and the Giga-Pack II Packaging Kit (Stratagene), after which the resulting phage was infected into E. coli strain LE392. The target gene was then cloned using the 5×10^4 phage library resulting from this method.

Example A4: Preparation of Long Chain Probe by PCR

A long probe amplified by PCR was prepared using the total DNA of Humicola insolens as a template, and this was used as the DNA probe.

DNA corresponding to the amino acids indicated with an asterisk on the N-terminal and peptide TP-3 were synthesized for each of the primers. The sequences of the prepared synthetic oligonucleotides were as shown below.

NCE4N1:5'-GCXGA(CT)GGXAA(AG)TC(AGCT)AC-3'(17mer) (SEQ ID NO:7)

NCE4N2:5'GCXGA(CT)GGXAA(AG)AG(CT)AC-3' (17mer) (SEQ ID No:8)

NCE4C: 5'CXGC(AG)TT(CT)TT(AG)AACCA(AG)TC-3'(19mer) (SEQ ID NO:9)

(X: inosine)

PCR reactions were conducted under the following conditions. To begin with, 2 pairs of tubes of 1 μM each of primers NCE4N1 and NCE4C added to 1 μg of Humicola insolens genome DNA, and 1μM each of primers NCE4N2 and NCE4C added to 1 μg of Humicola insolens genome DNA were prepared, and then subjected to thermal denaturation for 5 minutes at 95° C. in the presence of dNTP. Later, Taq polymerase (recombinant Taq, Takara Shuzo) was added to amplify by repeating 25 cycles under reaction conditions of 94° C. for 1 minute, 45° C. for 2 minutes and 72° C. for 3 minutes. As a result, approximately 750 bp DNA was amplified only in the case of using primers NCE4N1 and NCE4C. This was used as the probe in following screening.

Example A5: Cloning of Cellulase Component NCE4 Gene (1) Screening by Plaque Hybridization 100 ng of the approximately 750 bp DNA fragment amplified by PCR was labeled in advance by an ECL Direct DNA/RNA Labeling Detection System (Amersham).

The phage plaque prepared according to the method described in Example 2 was transferred to High-Bond N+Nylon transfer membrane (Amersham), and after denaturing with 0.4 N sodium hydroxide, it was washed with 5-fold concentrated SSC (15 mM trisodium citrate, 150 mM sodium chloride) and dried to fix the DNA. After pre-hybridizing (42° C.) for 1 hour according to the method of the kit, the previously labeled probe was added after which hybridization was performed for 4 hours (42° C.). Washing of the label was performed in accordance with method of the above kit. To begin with, washing was repeated twice for 20 minutes at 42° C. using 0.5-fold concentrated SSC containing 0.4% SDS and 6 M urea, followed by washing twice for 5 minutes at room temperature using 2-fold concentrated SSC.

After immersing the Nylon membrane from which the probe had been washed in the detection solution provided for 1 minute, it was photosensitized to Hyper-Film ECL (Amersham) to obtain four positive clones.

(2) Preparation of Phage DNA

E. coli LE392 was infected with a phage, the phage particles were collected 8 hours later, and after treating with proteinase K and phenol according to the method of Grossberger (Grossberger, D., Nucleic Acids Res. 15, 6737, 1987), the phage DNA was separated by ethanol precipitation.

(3) Subcloning of Target Gene

Four types of phage DNA were digested by Sal I and applied to agarose gel electrophoresis.

DNA was transferred to a Nylon membrane by the method of Southern (Southern, E.M., J. Mol. Biol., 98: 503–517, 1975), and hybridized using a probe of approximately 750 bp under the same conditions as the plaque hybridization of (1) above followed by detection of the 5.2 kbp DNA fragment containing the target gene. As a result, the four types of phage DNA has Sal I fragments of the same size.

This 5.2 kbp DNA fragment was separated using the Sephaglass Band Prep Kit (Pharmacia-Biotech) followed by subcloning to the Sal I site of plasmid pUC119 using E. coli JM109. The resulting plasmid was designated as pNCE4Sal.

Example A6: Determination of Base Sequence (1) Base Sequence Analysis of Genome DNA Determination of base sequence was performed in the manner described below.

The A. L. F. DNA Sequencer II (Pharmacia-Biotech) was used for the base sequence analyzer. Acrylamide carrier able to be acquired as Ready-Mix Gel (Pharmacia-Biotech) or Hydrolink Long Ranger (FMC) was used for the sequencing gel. A.L.F. grade reagents (Pharmacia-Biotech) were used for the various reagents used for gel preparation (N,N,N', N'-tetramethylethylenediamine, urea, ammonium persulphate). The Auto-Read Sequencing Kit (Pharmacia-Biotech) was used for the base sequence decoding reaction. Gel preparation conditions, reaction conditions and migration conditions were set by referring to the details of each instruction manual.

After alkaline-denaturing pNCE4Sal with 10µg of 2M sodium hydroxide to use it as a template DNA, it was annealed with the universal primer provided with the Auto-Read Sequencing Kit to perform an elongation reaction. After sequencing the reaction product with the sequencer, a 546 bp base sequence was sequenced. Based on this result, an FITC-labeled sequencing primer in the form of MNEG01 was prepared, reacted with pNCE4Sal followed by further sequencing. The following primer was then prepared based on the result obtained after which the entire length of NCE4 was decoded as a result of proceeding with decoding. The prepared FITC-labeled sequencing primers were as indicated below.

MNEG-01: 5'-GTGATGAGGGCTGGCGACAGGCC-3' (23mer) (SEQ ID NO:10)
MNEG-02: 5'-CTGCCACCTCTATTGCCGGCAGC-3' (23mer) (SEQ ID NO:11)
MNEG-03: 5'-CCCGACGCCCTCAAGCCCGGCTG-3' (23mer) (SEQ ID NO:12)
MNEG-04: 5'-GGCTGGAGCGGCTGCACCACCTG-3' (23mer) (SEQ ID NO:13)

(2) Base Sequence Determination

FITC-labeled sequencing primer DNA in the form of MNEG-05 through MNEG-08 were synthesized based on the results of (1) above. The prepared FITC-labeled sequencing primers were as indicated below.

MNEG-05: 5'-GACCTGACGGAAGCTGAAGCTCG-3' (23mer) (SEQ ID NO:14)
MNEG-06: 5'-AGCAGTGCAGCCGCTGGGAGTCG-3' (23mer) (SEQ ID NO:15)
MNEG-07: 5'-TGGCAGATGAGGACGTGGTGTTG-3' (23mer) (SEQ ID NO:16)
MNEG-08: 5'-CGCAGCCGGACTTGGCGTCGAAG-3' (23mer) (SEQ ID NO:17)

These primers were reacted with pNCE4Sal using the Auto-Read Sequencing Kit. First of all, 10 µg of plasmid were alkaline-denatured, annealed with each primer, and allowed to react with T7 polymerase. As a result, a 1257 bp base sequence was able to be determined in the Sal I fragment. This sequence was as shown in SEQ ID No. 3.

Example A7: Determination of Intron

Determination of intron was performed by preparing MRNA from Humicola insolens M200-1, synthesizing cDNA using reverse transcriptase, and comparing this with the genome base sequence to identify the same region.

(1)Isolation of Whole RNA

Humicola insolens MN200-1 was cultured for 2 days in cellulase-inducing medium, and preferable the previously mentioned (N) medium, followed by collection of the microorganisms by centrifugation (3500 rpm, 10 minutes). 2 g of the above microorganisms were washed with sterile water and crushed with a blender (Nihon Seiki, Homogenizer AM-3) while frozen with liquid nitrogen. The crushed microorganisms were then suspended in 10 ml of denaturing solution containing 4 M guanidine thiocyanate(4 M guanidine thiocyanate, 25 mM trisodium citrate, 0.5% sodiumN-laurylsarcosinate, 0.1 M mercaptoethanol). After stirring for several minutes at room temperature, the suspension was neutralized with 1 ml of 2 M sodium acetate (pH 4.5) and additionally stirred after adding 10 ml of TE saturated phenol. 2 ml of chloroform-isoamyl alcohol (24:1) were addedand after stirring well, the microorganism components denatured with phenol were removed by centrifugation (3500 rpm, 10 minutes). The upper layer (aqueous layer) was aspirated off and nucleic acids were precipitated with 10 ml of isopropanol. The resulted precipitate was then centrifuged (3500 rpm, 10 minutes) to recover the nucleic acids after which the precipitate was washed with 70% ethanol-water by additional centrifugation.

After dissolving this precipitate in 3.5 ml of TE, 880 µl of 10 M lithium chloride solution were added to the solution followed by refrigerating for 2 hours at 5° C. and centrifugation (12,000 rpm, 10 minutes) to recover the precipitate. This precipitate was washed with 70% ethanol and used as the whole RNA fraction. The recovered amount was 2.7 mg and the yield was 0.14%.

(2) Preparation of Poly A Tail+RNA(=mRNA)

Preparation of mRNA was performed using a mRNA purification kit (Pharmacia-Biotech).

To begin with, 1 mg of the whole RNA prepared in (1) above was dissolved in 1 ml of elution buffer followed by thermal denaturation treatment for 10 minutes at 65° C. After rapidly cooling in ice, 0.2 ml of sample buffer were added. The entire amount of this RNA solution was charged into an oligo (dT) cellulose column, and after washing the column three times with high-salt buffer and 3 times with low-salt buffer, eluted with elution buffer heated to 65° C. This column procedure was repeated twice and the resulting product was used as the mRNA fraction. The amount recovered was 19.2μg the yield was 2%.

(3) Synthesis of cDNA

Synthesis of cDNA was performed using a time-saver cDNA synthesis kit (Pharmacia-Biotech).

5 μg of MRNA were dissolved in 20μl of sample buffer. After thermal denaturing for 10 minutes at 65° C., dithiothreitol solution and oligo (dT) primer were both added to first strand synthesis mix and allowed to react for 1 hour at 37° C. Then, this entire amount was added to second strand mix and allowed to react for 30 minutes at 12° C. and then for 1 hour at 22° C., and the resulting product was used as cDNA.

(4) PCR Amplification of Cellulase NCE4 cDNA

Using 1 μg of the synthesized cDNA as a template, only the target cDNA was amplified by PCR. Oligonucleotide primers having the sequences indicated below were prepared for use as primers of the N- and C-terminals.

NCE4-CN:
5'-ATGCGTTCCTCCCCTCTCCTCCGCTCCGCC-3'
(30mer) (SEQ ID NO:18)

NCE4-CC:
5'-TACAGGCACTGATGGTACCAGTCATTAATC-3'
(30mer) (SEQ ID NO:19)

The PCR reaction was carried out under the following conditions. 1 μM each of primer was added to 1μg of *Humicola insolens* cDNA followed by thermal denaturation for 10 minutes at 94° C. in the presence of dNTP. Then, Taq polymerase (recombinant Taq, Takara Shuzo) was added to amplify by repeating 30 cycles under reaction conditions of 94° C. for 1 minute, 50° C. for 2 minutes and 72° C. for 3 minutes. As a result of performing agarose gel electrophoresis, the amplified fragment was determined to be 0.9 kbp in size. This was then concentrated by ethanol precipitation and cloned using a pT7 blue-T vector kit (Novagen). This plasmid was designated as pCNCE4.

(5) Analysis of cDNA Base Sequence

The sequencing reaction was performed using an Auto-Read Sequencing Kit in the same manner as previously described.

Plasmid pCNCE4 was alkaline-denatured with 2M sodium hydroxide and precipitated with ethanol. This single-strand plasmid was used as a template and allowed to react with T7 polymerase. The sequence was determined by performing reactions using the above synthetic primers MNEG01, MNEG02, MNEG03, MNEG04, MNEG05, MNEG06, MNEG07 and MNEG08 as well as the universal primer and reverse primer provided with the kit.

As a result, a single, 56 bp intron was present. The non-translated initiation sequence, its stop sequence, and the regulatory sequence within the intron in the sequence of SEQ ID No. 2 are as shown below (the numbers indicate the sequence position numbers of SEQ ID No. 2).

Intron: 453–458, 506–508, 491–497

Example A8: Evaluation of the Nap Removing Activity of NCE4 on Cellulose-Containing Fibers Pre-dyed Tencel fabric (Courtauls) was napped using a large washer adding surfactant and a rubber ball. Tencel in which nap were formed as a result of this treatment was removed of nap by cellulase treatment under the following conditions followed by calculation of the protein concentration of cellulase required to completely remove the nap.

Test machine: 20 kg washer (Sanyo, Fully-Automated Washing Machine SCW5101)

Bath ratio: 1:20

Heating: 55° C.

Time: 60 minutes pH: 7 (10 mM phosphate buffer)

In addition to cellulase enzyme liquid, rubber balls were added in an amount roughly twice the weight of the cloth to the treatment liquid.

TABLE 1

|  | Amt. of Protein Required to Remove Nap from Tencel* |
| --- | --- |
| NCE4 | 5 mg/liter |
| Crude Cellulase Preparation | 500 mg/liter |

*The amount of protein was quantified by using a protein assay kit (Biorad) and bovine serum albumin for the standard.

Based on the results, it was determined that NCE4 is able to demonstrate an equal degree of Tencel nap removal at a protein concentration $\frac{1}{100}$ that of crude cellulase preparation.

Example A9: Evaluation of Decoloring Activity of NCE4 on Denim-Dyed, Cellulose-Containing Fibers Destarched 12-ounce blue jeans were decolored under the conditions described below.

Test machine: 20 kg washer (Sanyo, Fully-Automatic Washing Machine SCW5101)

Bath ratio: 1:50

Heating: 55° C.

Time: 60 minutes pH: 7 (10 mM phosphate buffer)

In addition to cellulase enzyme liquid, rubber balls were added in an amount roughly twice the weight of the cloth to the treatment liquid.

Decoloring was determined by measuring the L value (lightness) of an Lab indication system using a color difference type of Color Analyzer Topscan Model TC-1800MK2 (Tokyo Denshoku). Representing the increase in L value relative to a control (increase in lightness) as the ΔL value, the ΔL values of 5 points for each test area evaluated for decoloring were measured (n=5), and the mean value of 3 points after discarding the maximum and minimum values was used. The protein concentration of cellulase required to decolor to a level of ΔL=7 was calculated.

TABLE 2

|  | Amt. of Protein Required to Discolor Blue Jeans |
| --- | --- |
| NCE4 | 1.8 mg/liter |
| Crude cellulase preparation | 45.0 mg/liter |

Based on these results, NCE4 was determined to be able to demonstrate an equal degree of discoloring of denim-dyed blue jeans at a protein concentration $\frac{1}{25}$ that of crude cellulase preparation.

Example A10: Evaluation of Weight Reduction Activity of NCE4 on Cellulose-Containing Fibers Enzyme treatment was performed on Cupra, Recycled cellulose fibers (Asahi Chemical Industry, 15 cm long×10 cm wide) for which absolute dry weight was measured in advance under the conditions indicated below.

Test machine: Washing resistance tester L-12 (Daiei Scientific Instruments)
Bath ratio: 1:50
Heating: 55° C.
Time: 60 minutes
pH: 7 (40 mM phosphate buffer)

In addition to cellulase enzyme liquid, stainless steel balls provided (Daiei Scientific Instruments) were added to the treatment liquid. Following enzyme treatment, the fibers were dried, the absolute dry weight of the Cupra fibers were measured, and the weight reduction ratio relative to before enzyme treatment was measured. The protein concentration of cellulase required to produce a weight reduction ratio of 8% was calculated.

TABLE 3

|  | Amt. of Protein Required for Cupra Weight Reduction of 8% |
| --- | --- |
| NCE4 | 100 mg/liter |
| Crude cellulase preparation | 500 mg/liter |

Based on these results, NCE4 was determined to be able to demonstrate an equal degree of weight reduction processing on Cupra fibers at a protein concentration ⅕ that of crude cellulase preparation.

Example B1: Construction of Plasmid pMKD01

(1) Construction of Plasmid pUC118BN

After cleaving 1 μg of pUC118 DNA with BamH I, the restriction enzyme was inactivated by treatment with phenol. This was then subjected to ethanol precipitation and dissolved in a small amount of TE (10 mM Tris-HCl (pH 8.0), 1 mM EDTA) buffer. The ends of this DNA were blunted with a DNA branching kit (Takara Shuzo). This was further ligated with a DNA ligation kit (Takara Shuzo) and allowed to self-close. The resulting ligated mixture was transformed into E. coli component cells JM109 (Takara Shuzo). Those transformants able to grow on LB agar medium (1% polypeptone, 0.5% yeast extract, 1% NaCl, 1.5% agar) containing 100 μg/ml of ampicillin, 1 mM IPTG and 0.004% of X-gal that also demonstrated white colonies were selected, and additionally cultured overnight at 37° C. in LB medium (1% polypeptone, 0.5% yeast extract, 1% NaCl) containing 100μg/ml of ampicillin. Plasmid DNA was recovered from the resulting culture liquid using alkaline-SDS. This plasmid DNA was cleaved with BamH I and applied to 0.8% agarose gel electrophoresis followed by selection of plasmid DNA in which the BamH I site of pUC118DNA was destroyed. This plasmid DNA was designated as pUC118BN.

(2) Construction of Plasmid pUC118BSN

1 μg of pUC118BN DNA was digested with Sph I and plasmid DNA was obtained in which the Sph I site of pUC118BN was destroyed according to the same method as described above. This plasmid DNA was designated as pUC118BSN.

(3) Construction of Plasmid pM21

A) Isolation of Cellulase NCE2 Gene

The cellulase NCE2 gene obtained from Humicola insolens according to the method described in Japanese Patent Laid-Open Publication No. 8-126492, and a Pst I-Xba I fragment of a total length 3.4 Kbp having a 1.4 Kb DNA sequence upstream and a 0.5 Kb DNA sequence downstream as its promoter and terminator regions, were ligated to the Pst I-Xba I site of the previous pUC118BSN. The resulting plasmid DNA was designated as pUC118BSN-PX.

B)Site-directed mutagenesis reaction of Plasmid pUC118BSN-PX

BamH I sites were introduced by site-specific mutation as described below downstream of the N-terminal and immediately downstream from the stop codon of NCE2 gene. E. coli JM109 strain was transformed by plasmid pUC118BSN-PX, and after additionally infecting with helper phage M13K07, culturing was performed for 16–20 hours at 37° C. in 30 ml of 2xYT liquid medium (1.6% bactotryptone, 0.8% yeast extract, 0.5% NaCl) containing ampicillin and kanamycin at concentrations of 150 μg/ml and 70μg/ml, respectively. Single-strand DNA of M13 (ssDNA) was recovered from the culture supernatant. Site-directed mutagenesis reaction was performed using this ssDNA and two types of synthetic oligonucleotides with the Sculpture In Vitro Mutagenesis System (Amersham). The sequences of the prepared synthetic oligonucleotide primers are as shown below.

MNC-02 5' -GAGCGCCAGAACTGTGGATCCACTTG GTGAGCAATG-3' (SEQ ID NO:20) (36mer)

MNC-03 5' -TCCGCCGTTCTGAGCGGATCCAGGCG TTTGGCGCG-3' (SEQ ID NO:21) (35mer)

The mixture of site-directed mutated DNA was introduced into E. coli TG1 and the resulting transformant was cultured in LB medium (1% polypeptone, 0.5% yeast extract, 1% NaCl) containing 100 μg/ml of ampicillin, followed by recovery of the plasmid DNA. This plasmid DNA was digested with BamH I and applied to 0.8% agarose gel electrophoresis followed by selection of plasmid DNA in which BamH I sites were introduced at two locations in plasmid pUC118BSN-PX. This plasmid DNA was designated as pM21.

(4) Isolation of The Cellulase NCE3 Gene

The cellobiohydrolase gene (NCE3) originating in Humicola insolens was isolated by PCR based on the sequence of known cellobiohydrolase gene originating in Humicola grisea (de Oliviera Alzevedo, M. et al., J. General Microbiol., 136: 2569–2576, 1990).

A) Isolation of Genome DNA

Genome DNA of Humicola insolens MN 200-1 was obtained by the method of previously described Example A3.

B) Amplification of The Cellulase NCE3 Gene by PCR

The NCE3 gene of Humicola insolens was isolated by PCR based on the sequence of cellobiohydrolase gene originating in Humicola grisea. Each primer was designed in advance in a form that contained a BamH I site so that the PCR product containing NCE3 is able to be ligated in line with the frame to the BamH I site of plasmid pM21. Synthetic oligonucleotides having the sequences shown below were prepared for use as primers.

MKA-05: 5'-GCCGCCCAGCAGGCGGGATCCCTCAC CACCGAGAGG-3'(36mer) (SEQ ID NO:22)

MKA-06: 5'-TGATCGTCGAGTCAGGGATCCAGAAT TTACAGGCAC-3'(36mer) (SEQ ID NO:23)

The PCR reaction was carried out according to the following method in accordance with the LA PCR Kit Ver. 2 (Takara Shuzo). To begin with, 1 μM of each primer, 400 μM dNTP and 2.5 U of LA Taq polymerase were added to 1μg of the Humicola insolens genome DNA obtained by the method described above followed by amplification by repeating 30 cycles under reaction conditions of 94° C. for 1 minute, 55° C. for 2 minutes and 72° C. for 3 minutes. As a result of 0.8% agarose gel electrophoresis, amplification of 1.6 Kbp DNA was confirmed. This 1.6 Kbp DNA fragment was recovered using a Sephaglass Band Prep Kit (Pharmacia-Biotech), and then ligated to pT7 blue-T vector kit (Novagen). This plasmid DNA was designated as pK21.

(5) Construction of Plasmid pKM04

Plasmid pK21 DNA was digested with BamH I and a 1.6 Kbp DNA segment was recovered. Then, plasmid pM21 DNA was digested with BamH I after which restriction enzyme was inactivated by treating for 10 minutes at 70° C. This was dephosphated with calf alkaline phosphatase (Takara Shuzo) and separated by 0.8% agarose gel electrophoresis followed by recovery of a 5.2 Kbp DNA fragment. The 1.6 Kbp DNA fragment originating in pK21 and the 5.2 Kbp DNA fragment originating in pM21 were ligated to obtain plasmid pKM04.

(6) Construction of Plasmid pMKD01

To begin with, a gene was prepared that allowed expression of the destomycin-resistant gene described in Japanese Patent Laid-Open Publication No. 59-175889 in Humicola insolens using the promoter and terminator of the trp C gene originating in *Aspergillus nidulans* obtained by known methods (Mullaney, E.J. et al., Mol. Gen. Genet., 199: 37–45, 1985). This gene was introduced into the Xba I site of plasmid pKMO4 to prepare plasmid pMKD01.

Example B2: Transformation of Humicola Insolens by Plasmid pMKD01

(1) Preparation of Highly Concentrated Purified Standard of Plasmid pMKD01

Highly concentrated purified standard of pMKDO1 was first prepared in order to introduce plasmid pMKDO1 into Humicola insolens. After introducing pMKD01 into *E. coli* JM109, it was cultured overnight at 37° C. in 100 ml of LB medium containing 100 µg/ml of ampicillin. The resulting culture liquid was purified using a Flexiprep Kit (Pharmacia-Biotech) to obtain 1 µg/µl of pMKD01 plasmid DNA.

(2) Transformation of Humicola Insolens

Humicola insolens MN200-1 was cultured at 37° C. in (S) medium after which the microorganisms were collected by centrifugation for 10 minutes at 3000 rpm 24 hours later. Here, the composition of the (S) medium consisted of adding glucose (3.0%) but omitting Avicel from the previously mentioned (N) medium. The resulting microorganisms were washed with 0.5 M sucrose and suspended in 10 ml of protoplastic enzyme solution filtered with a 0.45µm filter (5 mg/ml Novozyme 234 (NLI), 5 mg/ml Cellulase Onozuka R-10 (Yakult), 0.5 M sucrose). The mycelia were converted into protoplasts by shaking for 60 to 90 minutes at 30° C. After filtering this suspension, the protoplasts were recovered by centrifugation for 10 minutes at 2500 rpm and then washed with SUTC buffer (0.5 M sucrose, 10 mM calcium chloride, 10 mM Tris-HCl (pH 7.5)).

Protoplasts prepared in the above manner were suspended in 1 ml of SUTC buffer followed by the addition of 10µg of DNA (TE) solution (10µl) to 100 µl of this suspension and allowing to stand undisturbed for 5 minutes in ice. Then, 400µl of PEG solution (60% PEG4000, 10 mM calcium chloride, 10 mM Tris-HCl (pH 7.5)) were added, and after allowing to stand undisturbed for 20 minutes in ice, 10 ml of SUTC buffer were added followed by centrifugation for 10 minutes at 2500 rpm. After suspending the collected protoplasts in 1 ml of SUTC buffer, they were again centrifuged for 5 minutes at 4000 rpm and finally suspended in 100 µl of SUTC buffer.

Protoplasts subjected to the above treatment were layered with YMG soft agar over YMG medium containing 200 µg/ml of hygromycin B (1% glucose, 0.4% yeast extract, 0.2% malt extract, 1% agar (pH 6.8)), and after culturing for 5 days at 37° C., the formed colonies were used as transformants.

(3) Culturing of pMKD01 Transformed Strains and Evaluation by SDS-PAGE

Plasmid pMKD01 was introduced into Humicola insolens MN200-1 as previously described followed by selection of 50 strains exhibiting resistance to hygromycin. These were cultured for 5 days at 37° C. in (N) medium. When the resulting culture supernatant was analyzed by SDS-PAGE, in 5 clones of pMKD01 transformed strains, the protein band estimated to be NCE3 was increased 3–4 times higher than the parent strain.

(4) Identification of N-Terminal Amino Acid Residues of Recombinant NCE3

In order to confirm that the protein band expressed in large amounts originated in the NCE3 gene based on the results of SDS-PAGE, the N-terminal amino acid sequence of this protein was determined. To begin with, column chromatography was performed on the culture supernatants obtained from the parent strain and NCE3 high-expression strains using an FPLC system in accordance with the method of the previously described Example A2, followed by comparison of the major peaks. The peak that was particularly increased in the NCE3 high-expression strains was removed and lyophilized. This was dissolved in a small amount of water followed by electrophoresis using 8% Gel SDS-PAGE Mini (Difco). The protein was then electrically transferred to a PVDF membrane according to the method of Example A2 above, and after staining with Coomassie brilliant blue R-250, the membrane was decolored and washed with water. A portion in which a protein having a molecular weight of 66 KD was blotted was cut out from this membrane, and the modified N-terminal residues were removed from the blotted protein according to the method of Podell, D. N. et al. (Podell, D. N., et al., Biochem. Biophys. Res. Commun., 81: 176, 1978). First of all, the target protein was cut out, and after incubating for 30 minutes at 37° C. in a small amount of 0.5% polyvinylpyrrolidone (molecular weight: 40,000, Sigma)/100 mM acetic acid solution, was washed well with water. Then, the modified N-terminal residues were removed by Pfu pyroglutamate aminopeptidase (Takara Shuzo), washed with water and air dried. This was then applied to a Model 492 Protein Sequencer to determine 15 residues of the N-terminal amino acid sequence. The resulting sequence is shown below.

N-terminal amino acid sequence: Asn-Cys-Gly-Ser-Leu-Thr-Thr-Glu-Arg-His-Pro-Ser-Leu-Ser-Trp (15 residues) (SEQ ID NO:24)

This N-terminal amino acid sequence coincided with the cellulase NCE2 and NCE3 fused protein amino acid sequence estimated from the base sequence of plasmid pMKD01.

(5)FPLC Evaluation of pMKD01 Transformed Strains

As was previously described, column chromatography was performed using an FPLC system to further quantify the culture supernatants of the 5 clones confirmed to express large amounts of NCE3 by SDS-PAGE. The conditions were the same as in (4) above. The NCE3 peak was removed and lyophilized, and the weight was measured and the productivity was compared between high expression strains and the parent strain. Those results were as shown in the table below.

TABLE 4

| | NCE3 Productivity* |
|---|---|
| Humicola insolens MN200-1 (parent strain) | 0.46 g |
| Humicola insolens pMKD01 | 1.8 g |

*Productivity refers to the amount produced per one liter of culture liquid.

Example B3: Construction of Plasmid pEGD01

Plasmid pMKD01 was digested with BamH I and restriction enzyme was inactivated by heat treatment at 70° C. after which it was dephosphated to recover an 8.2 Kbp DNA fragment.

Then, the NCE4 gene was amplified by PCR based on the sequence of the NCE4 gene originating in Humicola insolens obtained in the above Examples A1 through A7. This PCR product containing NCE4 was designed in a form in which each primer contained a BamH I site in advance so that it could be ligated while aligning the frame with the 8.2 Kbp BamH I fragment of the above plasmid pMKD01. Synthetic oligonucleotides having the sequences shown below were prepared for use as primers.

NCE4-N:
5'-CCGGTGTTGGCCGGATCCGCTGATGGCAAG-3'(30mer) (SEQ ID NO:25)

NCE4-C:
5'-TAAGGCCCTCAAGGATCCCTGCGTCTACAG-3'(30mer) (SEQ ID NO:26)

The PCR reaction was carried out in the following manner. 1 μM of each primer, 400μM dNTP and 2.5 U of Pfu DNA polymerase (Stratagene) were added to 1μg of Humicola insolens genome DNA, and a 0.8 Kbp DNA fragment was amplified by repeating 25 cycles of reaction conditions consisting of 94° C. for 1 minute, 55° C. for 2 minutes and 72° C. for 3 minutes. This 0.8 Kbp DNA fragment was recovered and ligated to the above 8.2 Kbp BamH I fragment of pMKD01. This plasmid DNA was designated as pEGD01.

Example B4: Expression of Plasmid pEGD01

(1) Transformation of Humicola Insolens by Plasmid pEGD01

Transformation of Humicola insolens MN200-1 by plasmid pEGD01 was performed in accordance with the method of Example B2. To begin with, a highly concentrated and purified standard of pEGD01 was prepared to obtain 1μg/μl of pEGD01 plasmid DNA. *Humicola insolens* MN200-1 was transformed using 10μl of this pEGD01 solution followed by selection of 50 transformant strains exhibiting resistance to hygromycin. These were cultured for 5 days at 37° C. in (N) medium. When the resulting culture supernatant was analyzed by SDS-PAGE, the protein band estimated to be NCE4 was increased 10–16 times more than in the parent strain in 10 clones of the strains transformed by pEGD01.

(2) Identification of N-Terminal Amino Acid Residues of Recombinant NCE4

In order to confirm that protein band expressed in large amounts originated in the NCE4 gene based on the results of SDS-PAGE, the N-terminal amino acid sequence of this protein was determined. To begin with, column chromatography was performed on the culture supernatants obtained from the parent strain and NCE4 high-expression strains using an FPLC system followed by comparison of the major peaks. The conditions were the same as in the above Example B2. The peak that was particularly increased in the NCE4 high-expression strains was removed and lyophilized. This was dissolved in a small amount of water. After removing the modified N-terminal residues according to the method of Example B2, the N-terminal amino acid sequence was determined using the above protein sequencer. As a result, two types of N-terminal amino acid sequences were obtained in a ratio of about 7:3. The resulting sequences were as shown below. Then, the N-terminal amino acid sequence was determined using the same protein sequencer without removing the modified N-terminal. As a result, only amino acid sequence 1 was obtained as shown below.

N-terminal amino acid sequence 1: Val-Val-Glu-Glu-Arg-Gln-Asn-Cys-Gly-Ser-Ala-Asp-Gly-Lys-Ser-Thr-Arg-Tyr-Trp-Asp (20 residues) (SEQ ID NO:27)

N-terminal amino acid sequence 2: Asn-(Cys)-Gly-Ser-Ala-Asp-Gly-Lys-Ser-Thr-Arg-Tyr-Trp-Asp-(Cys)-(Cys)-Lys-Pro-Ser-(Cys) (20 residues) (SEQ ID NO:28)

These N-terminal amino acid sequences coincided with the cellulase NCE2 and NCE4 fused protein amino acid sequence estimated from the base sequence of plasmid pEGD01. Since two types of N-terminal amino acid sequences were obtained, it was clearly shown that when the signal sequence of this fused protein is cleaved, it is processed at a plurality of sites.

(3) FPLC Evaluation of pEGD01 Transformed Strains

As was previously described, column chromatography was performed using an FPLC system to further quantify the culture supernatants of the 5 clones confirmed to express large amounts of NCE4 by SDS-PAGE, and the NCE4 peak was removed. This was then lyophilized, and the weight thereof was measured and the productivity was compared between high expression strains and the parent strain. Those results were as shown in the table below.

TABLE 5

| | NCE4 Productivity* |
|---|---|
| Humicola insolens MN200-1 (parent strain) | 0.28 g |
| Humicola insolens pEGD01 | 4.5 g |

*Productivity refers to the amount produced per one liter of culture liquid.

Example B5: Construction of Plasmid pIED02

(1) Construction of Plasmid pID01

Plasmid pEGD01 was digested with Hind III and BamH I and a 7.2 Kbp DNA fragment was recovered.

Then, the portion of DNA that codes for the promoter and signal sequences of NCE1 gene was amplified by PCR based on the sequence of NCE1 gene originating in the Humicola insolens obtained with the method described in Japanese Patent Laid-Open Publication No. 8-56663. This PCR product that contains NCE1 promoter and signal sequence was designed in a form in which each primer contains an Hind III and BamH I site in advance so that it can be ligated to the 7.2 Kbp Hind III to BamH I fragment of the above plasmid pEGDO1. Synthetic oligonucleotides having the sequences shown below were prepared for use as primers.

PNCE1-N: 5'-GTCATGAAGCTTCATTAAGGTACGTA TGCAAC-3'(32mer) (SEQ ID NO:29)

PNCE1-C: 5'-GGTGATGGATCCGGCCTGCTGGGCAG CGACGC-3'(32mer) (SEQ ID NO:30)

The PCR reaction was carried out in the same method as Example B3. 1 μM of each primer, 400 μM dNTP and 2.5 U of Pfu DNA polymerase were added to 1 μg of *Humicola insolens* genome DNA, and a 1.5 Kbp DNA fragment was amplified by repeating 23 cycles of reaction conditions consisting of 94° C. for 1 minute, 55° C. for 2 minutes and 72° C. for 4 minutes. This 1.5 Kbp DNA fragment was recovered by digesting the PCR product with Hind III and BamH I. It was then ligated to the above 7.2 Kbp Hind III to BamH I fragment of pEGD01. This plasmid DNA was designated as pID01.

(2) Construction of Plasmid pIED02

Plasmid pID01 was digested with BamH I and restriction enzyme was inactivated by heat treatment at 70° C. after which it was dephosphated to recover an 8.6 Kbp DNA fragment. Then, after digesting plasmid pEGD01 with BamH I, a 0.8 Kbp DNA fragment was recovered that contained NCE4 gene. The two fragments were ligated to obtain plasmid pIED02.

Example B6: Expression of Plasmid pIED02

(1) Transformation of Humicola Insolens by Plasmid pIED02

Transformation of Humicola insolens MN200-1 by plasmid pIED02 was performed in accordance with the method of Example B2. To begin with, a highly concentrated and purified standard of pIED02 was prepared to obtain 1 μg/μl of pIED02 plasmid DNA. *Humicola insolens* MN200-1 was transformed using 10 μl of this pIED02 solution followed by selection of 50 transformant strains exhibiting resistance to hygromycin. These were cultured for 5 days at 37° C. in (N) medium. When the resulting culture supernatant was analyzed by SDS-PAGE, the protein band estimated to be NCE4 was increased 5–10 times more than in the parent strain in 5 clones of the strains transformed by pIED02.

(2) Identification of N-Terminal Amino Acid Residues of Recombinant NCE4

In order to confirm that protein band expressed in large amounts originated in NCE4 gene based on the results of SDS-PAGE, the N-terminal amino acid sequence of this protein was determined. To begin with, according to the method of Example B2 column chromatography was performed on the culture supernatants obtained from the parent strain and the NCE4 high-expression strains, after which the NCE4 peak was removed and lyophilized. This was dissolved in a small amount of water. After removing the modified N-terminal residues according to the method of Example B2, 15 residues of the N-terminal amino acid sequence were determined using the above protein sequencer. The resulting sequence was as shown below.

N-terminal amino acid sequence: Gln-Ala-Gly-Ser-Ala-Asp-Gly-Lys-Ser-Thr-Arg-Tyr-Trp-Asp-(Cys) (15 residues) (SEQ ID NO:29)

This N-terminal amino acid sequence coincided with the cellulase NCE1 and NCE4 fused protein amino acid sequence estimated from the base sequence of plasmid pIED02.

(3) FPLC Evaluation of pIED02 Transformed Strains

As was previously described, column chromatography was performed using an FPLC system to further quantify the culture supernatants of the 5 clones confirmed to express large amounts of NCE4 by SDS-PAGE, and the NCE4 peak was removed. This was then lyophilized, and the weight was measured and the productivity was compared between high expression strains and the parent strain. Those results were as shown in the table below.

TABLE 6

| | NCE4 Productivity* |
|---|---|
| Humicola insolens MN200-1 (parent strain) | 0.28 g |
| Humicola insolens pIED02 | 2.9 g |

*Productivity refers to the amount produced per one liter of culture liquid.

What is claimed is:

1. An isolated and purified enzymatically active fragment of a protein having an amino acid sequence from position 1 to position 284 of the amino acid sequence shown in SEQ ID No. 1.

2. The isolated and purified enzymatically active fragment of a protein according to claim 1 further comprising at least a portion of the amino acid sequence from position −21 through −1 shown in SEQ ID No. 1 at N-terminus thereof.

3. An isolated DNA fragment encoding the enzymatically active fragment of a protein according to claim 1.

4. The DNA sequence according to claim 3, wherein the DNA sequence has a portion or all of the base sequence shown in SEQ ID No. 2.

5. The DNA sequence according to claim 4, having a base sequence from position 118 to position 1088 of the base sequence shown in SEQ ID No. 2.

6. A vector comprising the DNA sequence according to claim 3.

7. A host cell transformed by the vector according to claim 6.

8. A method for preparing a protein having an amino acid sequence from position 1 to position 284 of the amino acid sequence shown in SEQ ID No. 1, comprising the steps of culturing a host cell transformed by a vector comprising a DNA sequence encoding the protein, and collecting the protein from the culture.

9. A cellulase preparation comprising an isolated protein having an amino acid sequence from position 1 to position 284 of the amino acid sequence shown in SEQ ID No. 1.

10. A method for removing nap of cellulose-containing fibers, the method comprising contacting cellulose-containing fibers with a protein according to claim 1.

11. A method for decoloring denim-dyed, cellulose-containing fibers, the method comprising contacting denim-dyed, cellulose-containing fibers with a protein according to claim 1.

12. A method for reducing cellulose-containing fibers, the method comprising contacting cellulose-containing fibers with a protein according to claim 1.

13. A method for removing nap of cellulose-containing fibers, the method comprising contacting cellulose-containing fibers with the cellulase preparation according to claim 9.

14. A method for decoloring denim-dyed, cellulose-containing fibers, the method comprising contacting denim-dyed, cellulose-containing fibers with the cellulase preparation according to claim 9.

15. A method for reducing cellulose-containing fibers, the method comprising contacting cellulose-containing fibers with the cellulase preparation according to claim 9.

16. An isolated and purified protein having endoglucanase activity consisting of the amino acid sequence from position 1 to position 284 of the amino acid sequence shown in SEQ ID No. 1 and at least part of the amino acid sequence from position −21 through −1 shown in SEQ ID No. 1 at N-terminus thereof.

17. A cellulase preparation comprising the isolated and purified protein according to claim 16.

18. A method for treating cellulose-containing fibers, the method comprising contacting the cellulase preparation according to claim 17 with cellulose-containing fibers.

19. A composition containing a protein in an amount effective for degrading cellulose, said protein having been isolated and purified and corresponding to the amino acid sequence shown in SEQ ID No. 1.

* * * * *